(12) United States Patent
Kashmirian (10) Patent No.: US 9,743,874 B2
(45) Date of Patent: Aug. 29, 2017

(54) LIQUID SAMPLING DEVICE WITH PASSIVE SAFETY

(71) Applicant: ikashmore Pty Ltd, Kambah, Australian Capital Territory (AU)

(72) Inventor: Avtar Kashmirian, Kambah (AU)

(73) Assignee: IKASHMORE PTY LTD, Kambah, Australian Capital Territory (AU)

( * ) Notice: Subject to any disclaimer, the term of this patent is extended or adjusted under 35 U.S.C. 154(b) by 286 days.

(21) Appl. No.: 14/420,639

(22) PCT Filed: Jul. 26, 2013

(86) PCT No.: PCT/AU2013/000829
§ 371 (c)(1),
(2) Date: Feb. 9, 2015

(87) PCT Pub. No.: WO2014/022878
PCT Pub. Date: Feb. 13, 2014

(65) Prior Publication Data
US 2015/0216464 A1 Aug. 6, 2015

(30) Foreign Application Priority Data
Aug. 10, 2012 (AU) .............................. 2012903434

(51) Int. Cl.
*A61B 5/15* (2006.01)
*G01N 1/20* (2006.01)
(Continued)

(52) U.S. Cl.
CPC ........ *A61B 5/150633* (2013.01); *A61B 5/153* (2013.01); *A61B 5/150343* (2013.01);
(Continued)

(58) Field of Classification Search
CPC . A61B 5/150633; A61B 5/153; A61B 1/2037; A61B 1/145
See application file for complete search history.

(56) References Cited

U.S. PATENT DOCUMENTS

| 2001/0025671 | A1 | 10/2001 | Safabash |
| 2005/0107765 | A1 | 5/2005 | Kashmiran et al. |
| 2011/0139276 | A1 | 6/2011 | Kashmiran et al. |

FOREIGN PATENT DOCUMENTS

WO 2011/140596 A1 11/2011

OTHER PUBLICATIONS

Patent Examination Report No. 1 (AU 2013302208); Date of Issue: Nov. 10, 2016.
(Continued)

*Primary Examiner* — Leslie Deak
(74) *Attorney, Agent, or Firm* — Howard & Howard Attorneys PLLC (57) ABSTRACT

A sampling device including a body (101) having a sampling chamber (102) adapted to receive a liquid (103) to be sampled. An inlet (104) on the body (101) allows liquid (103) to flow into the sampling chamber (102). A sampling port (105) on the body is adapted to receive a sampling pot or sample receiving container (106) for collecting liquid (103) from the sampling chamber (102) wherein the sampling port includes a safety shield (107) slidaby mounted to the inside (108) of the sampling port, the safety shield slidable between a blocking position in which access to the sampling chamber is restricted and an accessible position in which access to the sampling chamber is allowed.

17 Claims, 11 Drawing Sheets

(51) Int. Cl.
*A61B 5/153* (2006.01)
*G01N 1/10* (2006.01)
(52) U.S. Cl.
CPC ... *G01N 1/2035* (2013.01); *G01N 2001/1031* (2013.01); *G01N 2001/1037* (2013.01); *G01N 2001/2071* (2013.01)

(56) References Cited

OTHER PUBLICATIONS

International Search Report (PCT/AU2013/000829); Date of Mailing: Oct. 29, 2013.

LIQUID SAMPLING DEVICE WITH PASSIVE SAFETY

CROSS REFERENCE TO RELATED APPLICATION

This application is a national stage application of PCT/AU2013/000829, filed Jul. 26, 2013, which claims priority to Australian Patent Application No 2012903434, filed Aug. 10, 2012, the disclosures of which are hereby incorporated by reference in their entirety.

FIELD OF THE INVENTION

This invention relates to methods and apparatus for the prevention of needlestick injuries and other similar injuries during sterile sampling of liquids using tube barrel holders incorporating needles, cannulas or multi-sampling luer needles. It may be applied to tube barrel holders used in blood collection procedures and blood collection kits, tube barrel holders used for the transfer of platelets or other bodily fluids for sampling, testing or bacterial detection, in tube barrel holders used for collection of blood samples from patients for testing purposes using test tubes or evacuated tubes or in tube barrel holders used for accessing sampling ports, or for tube barrel holders for other containers like evacuated bottles or similar, but it would be understood that its application is not limited to this particular field of use and may be used in manufacturing environments such as laboratory, pathology and clinical environments and the like.

For convenience and without meaning to exclude other forms of containers, the liquid containers to be sampled will herein be called pouches. As it will be normal for the pouch being sampled to be arranged above the sampling apparatus to take advantage of the hydrostatic head thus provided, it will be convenient to refer to parts of the apparatus as being above or below, or as being upper or lower, with respect to other parts. However, the pouch and sampling apparatus could be arranged so liquid flow does not flow under gravity, in which case some parts are likely to be more distal or proximal relative to other parts (with respect to the user). Accordingly, the terms 'upper' and 'lower', 'above' and 'below' should be understood as being equivalent to 'distal' and 'proximal' (respectively) as used herein.

BACKGROUND OF THE INVENTION

In this specification unless the contrary is expressly stated, where a document, act or item of knowledge is referred to or discussed, this reference or discussion is not an admission that the document, act or item of knowledge or any combination thereof was at the priority date, publicly available, known to the public, part of common general knowledge; or known to be relevant to an attempt to solve any problem with which this specification is concerned.

Tube barrel holders are devices commonly used to allow one or more samples of liquid like blood or similar from patients or pouches to be collected directly into sample receiving containers in an essentially sterile manner or in a manner that reduces contamination. Tube barrel holders generally consist of a sampling chamber consisting of a needle, sheathed needle or multisampling needle and a sampling port that allows suitable sample receiving containers to be used with the tube barrel holders. The sample receiving containers may or may not be evacuated and generally have an elastomeric material in the cap or lid that allows the needle in the tube barrel holder to pierce thereby allowing the liquid sample to flow into the sample receiving container from the pouch, patient or other liquid bearing container. Sample receiving containers include tubes, phials, bottles and other similar containers. Each sample of liquid may vary from a quantity as little as 1 ml to 10 mls or more depending on the application and requirements.

There are occasions in clinical practice where it is desirable to check the sterility or other properties of a liquid stored in a pouch before that liquid is administered to a patient or otherwise used. Examples are blood and blood components such as serum and platelets. However, there is a danger that the sampling procedure in which a sample of the liquid is taken from the pouch can contaminate the liquid and introduce bacteria into the pouch and the liquid. Tube barrel holders are often used directly with the pouch via suitable access ports or in conjunction with other sampling devices to obtain samples of liquid for the required testing.

In other environments, such as manufacturing and the like, there is also the need to extract samples from a batch of liquid while ensuring the integrity of the batch.

In other occasions, it is desirable to obtain samples of blood from patients for testing or other purposes in a sterile manner and this is often conducted using tube holders in conjunction with venipuncture needles or scalp-vein needles.

The tube holders containing the sampling needles present an accidental needlestick hazard for healthcare and other workers as the mouth of the sample port is generally sufficiently large for fingers to enter the port and be exposed to the contaminated needle.

One method of reducing this needlestick injury risk is to provide a lid at the mouth of the sampling port that can be closed shut by the healthcare worker after the procedure has been completed. The present invention provides an automatic means of blocking access to the sampling needle that does not require intervention by the healthcare worker other than to complete the procedure by removing the sample receiving container from the tube barrel holder.

SUMMARY OF THE INVENTION

Throughout the specification and claims which follow, unless the context requires otherwise, the word "comprise", and other variations such as "comprises" and "comprising", will be understood to imply the inclusion of a stated integer or step or group of integers or steps but not the exclusion of any other integer or step or group of integers of steps.

It would be understood that preferred embodiments of the present invention overcome or ameliorate at least one of the disadvantages of the prior art, or at least provide a useful alternative.

According to a first aspect of the invention there is provided a sampling device including:
a body having a sampling chamber adapted to receive a liquid to be sampled;
an inlet on the body for allowing liquid to flow into the sampling chamber;
a sampling port on the body adapted to receive a sample receiving container for collecting liquid from the sampling chamber wherein the sampling port includes a safety shield slidaby mounted to the inside of the sampling port, the safety shield slidable between a blocking position in which access to the sampling chamber is restricted and an accessible position in which access to the sampling chamber is allowed. In other embodiments the shield is hinged or flexes between a blocking and an accessible position.

According to an alternative embodiment the invention provides a sampling port having two ends; the first end being adapted to receive a sampling bottle, phial, vacuum tube, test tube or other container for collecting liquid; the second end adapted for insertion into the sampling port of a needle, cannula or multi-sampling luer needle (sheathed needle) or a combination thereof.

Preferably the sampling chamber includes a cylindrical tube through which the liquid flows from the sampling chamber to the sample receiving container.

Preferably the cylindrical tube is a needle or cannula. In some embodiments the needle is sheathed or unsheathed and the cannula is controlled by say a stop cock. Preferably the safety shield prevents access to the sheathed needle until such time as a sample receiving container is inserted into the sample port.

Preferably the safety shield includes an aperture through which the needle can move when the safety shield moves into the accessible position. That is, when moving from the blocking position to the accessible position, the safety shield slides down towards the needle, the needle passes through the aperture in the safety shield allowing the needle to engage with a sample receiving container thereby allowing a sample to be taken.

Preferably the safety shield is locked in the blocking position until a suitable sample receiving container is inserted into the sampling port.

Preferably the locking is provided by one or more locking clips or locking tabs that prevent the safety shield from sliding down towards the needle and the base of the sampling port.

Preferably the locking clip or clips are located on the sampling port or on the shield. Preferably the sampling port includes five locking clips substantially equally spaced around the inside perimeter of the sampling port. Preferably the sample receiving container unlock the locking clips thereby allowing the safety shield to be pushed back over the needle and thereby allowing a sample to be taken when a sample receiving container is inserted into the sampling port. Preferably the shoulders, neck or other part of the sample receiving container is used to unlock the safety shield. As would be understood any suitable part of the bottle could be used to unlock the safety shield.

Preferably the safety shield includes a spring that forces the safety shield into the blocking position when the sampling bottle is removed. In other embodiments the act of removing the sample receiving container at the end of the sampling procedure may be used to return the shield into the locked position by incorporating simple grippers on the shield to hold onto the sample receiving container. Alternatively in a different design, the shield is attached to the sampling port rather than sliding, and it either flexes or hinges out of the way when the shield is un-locked.

Preferably the locking clips automatically engage the safety shield once the safety shield is returned to the blocking position. The automatic return of the safety shield to the blocked and locked position is considered as passive safety as it does not require the user to undertake any additional steps to make the device safe during and at the completion of the procedure, and is the most preferred form of safety in the medical industry.

The preferred embodiment of the present invention provides a device and method that allows samples of a liquid from a pouch commonly used in medical environments, blood sets, aphaeresis sets or directly from patients to be taken with minimal danger of needlestick injuries to the healthcare and other workers.

In some embodiments the sampling device includes an insert adapted on one end to fit in the sampling port and adapted on the other end to fit a sample receiving container wherein the insert disengages the locking clips. This allows sample receiving containers that have a smaller diameter to be used with embodiments of the invention and to thereby disengage the safety shield using the insert. Preferably the insert is circular and fits onto a mouth of the sampling port and disengages the locking clips. This then allows evacuated tubes to be used with the larger diameter sampling device.

Variations of the apparatus disclosed in the specification may be incorporated in products by manufacturers of blood collection sets, aphaeresis kits, urinary catheter kits, plural and abdominal cavity aspiration kits and the like.

DETAILED DESCRIPTION OF THE PREFERRED EMBODIMENT

Figure 1:
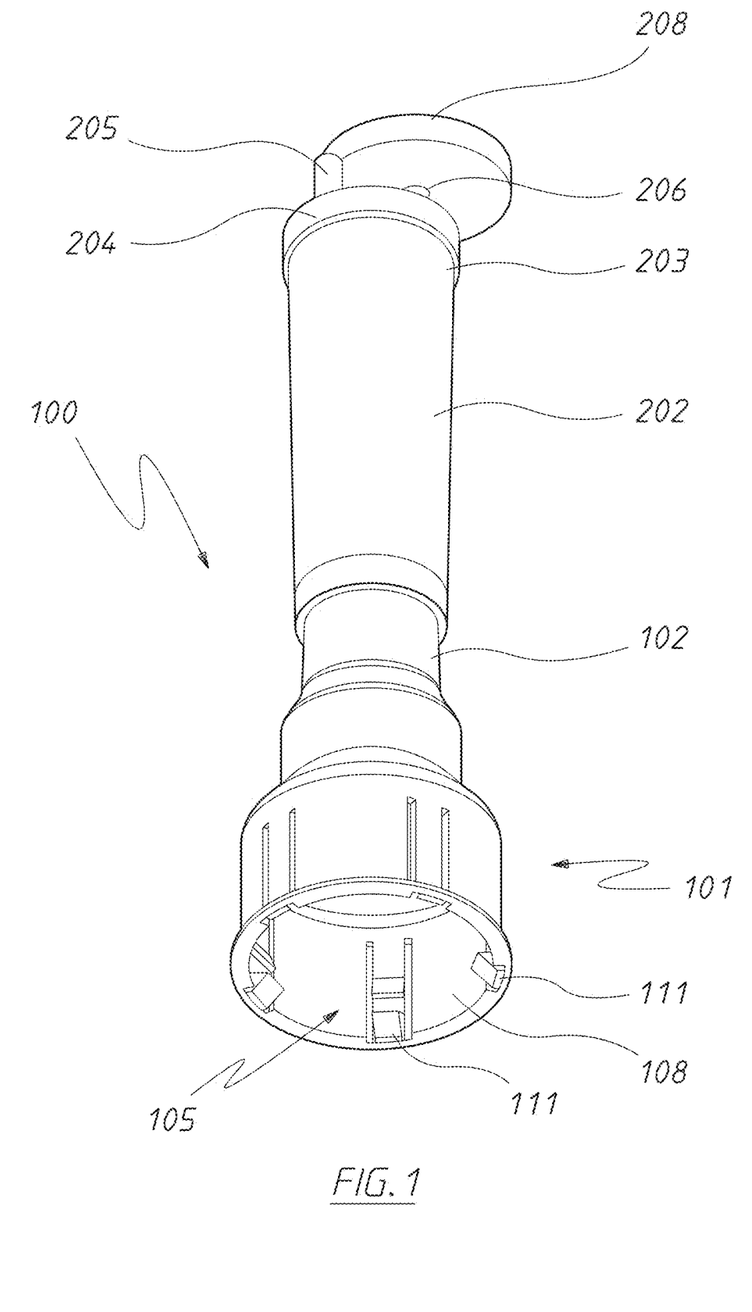
FIG. 1 is a view of a device according to the preferred embodiment of the invention.
Figure 2:
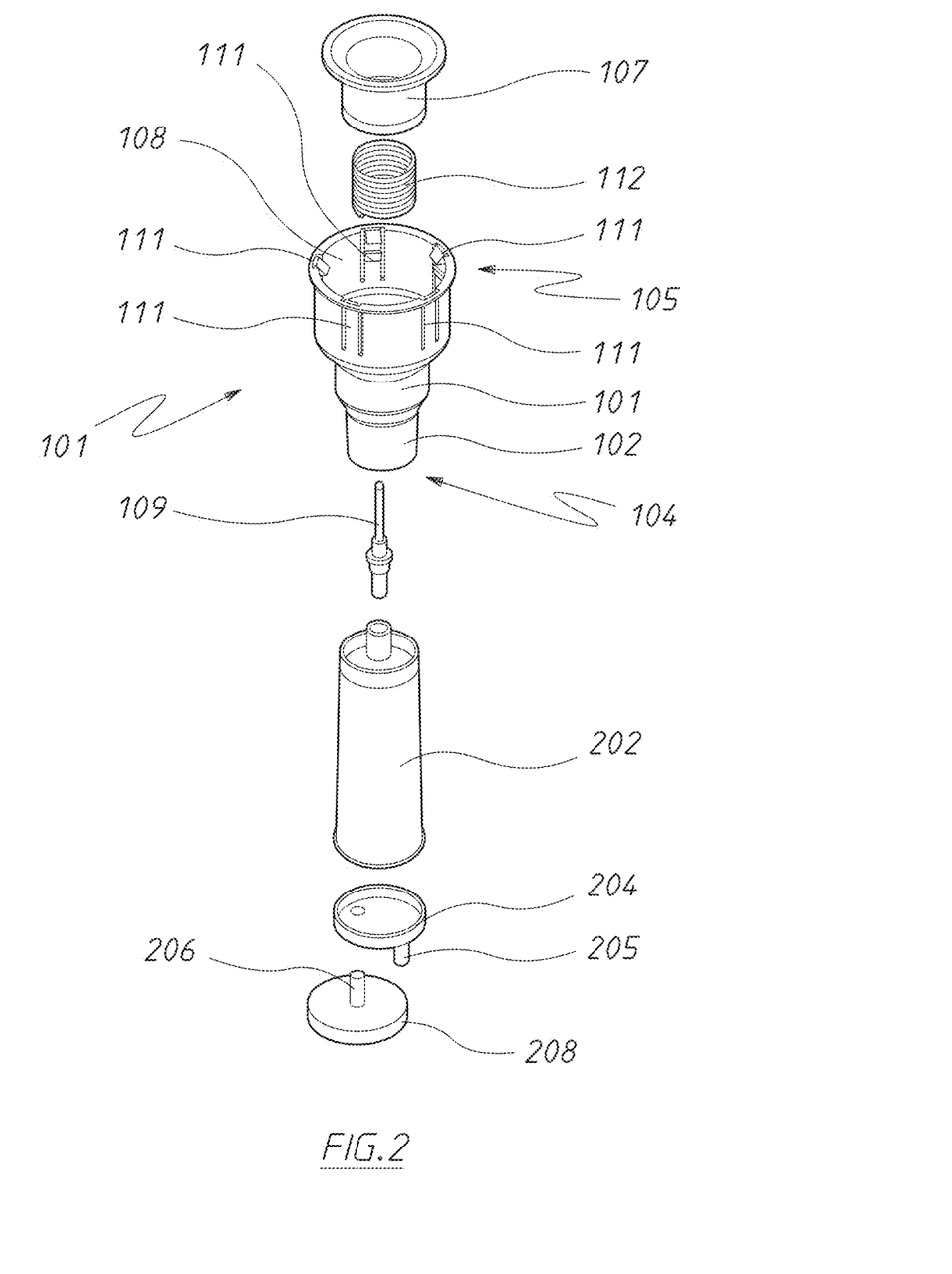
FIG. 2 is an exploded view of the device of FIG. 1.
Figure 3:
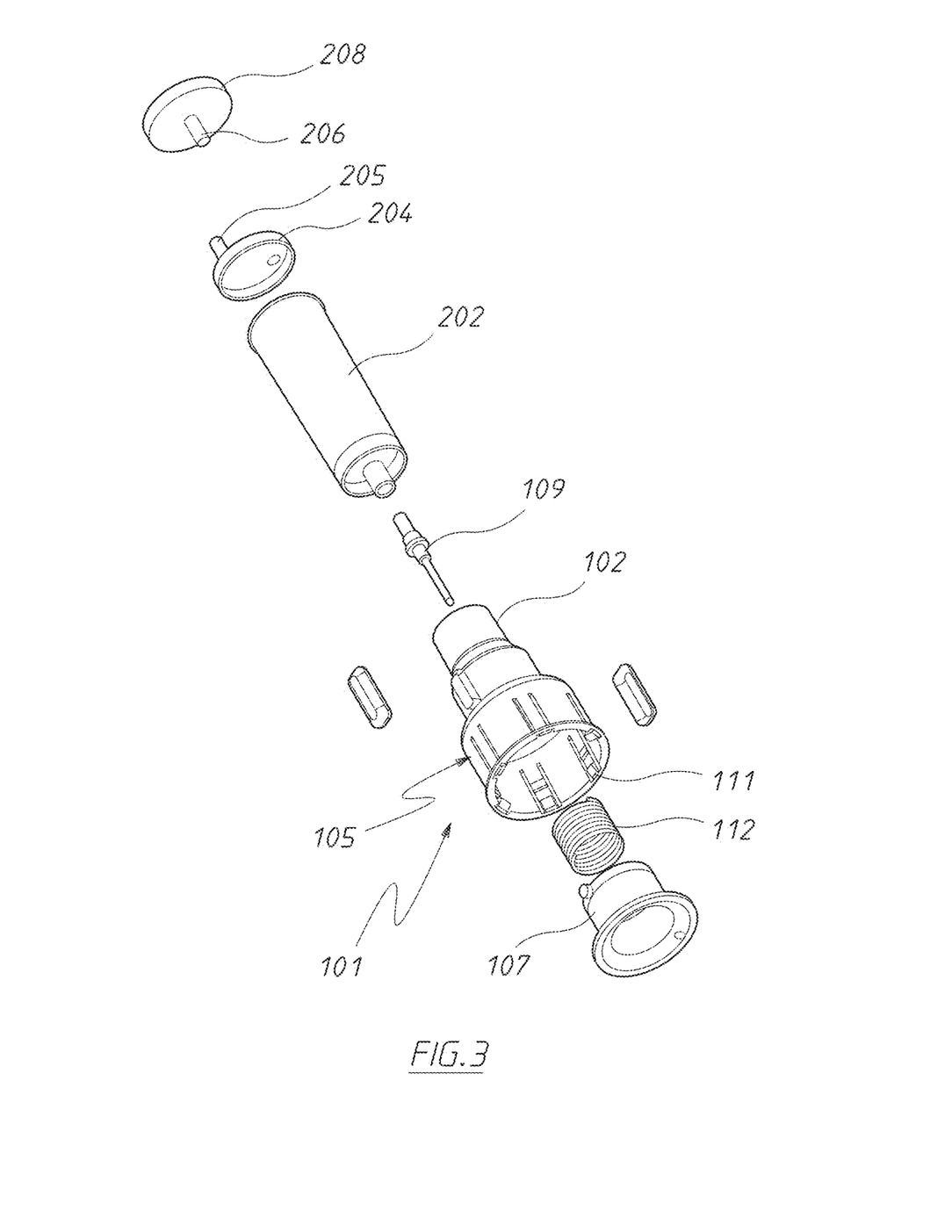
FIG. 3 is a perspective view of a sampling apparatus according to the preferred embodiment of the invention.
Figure 4:
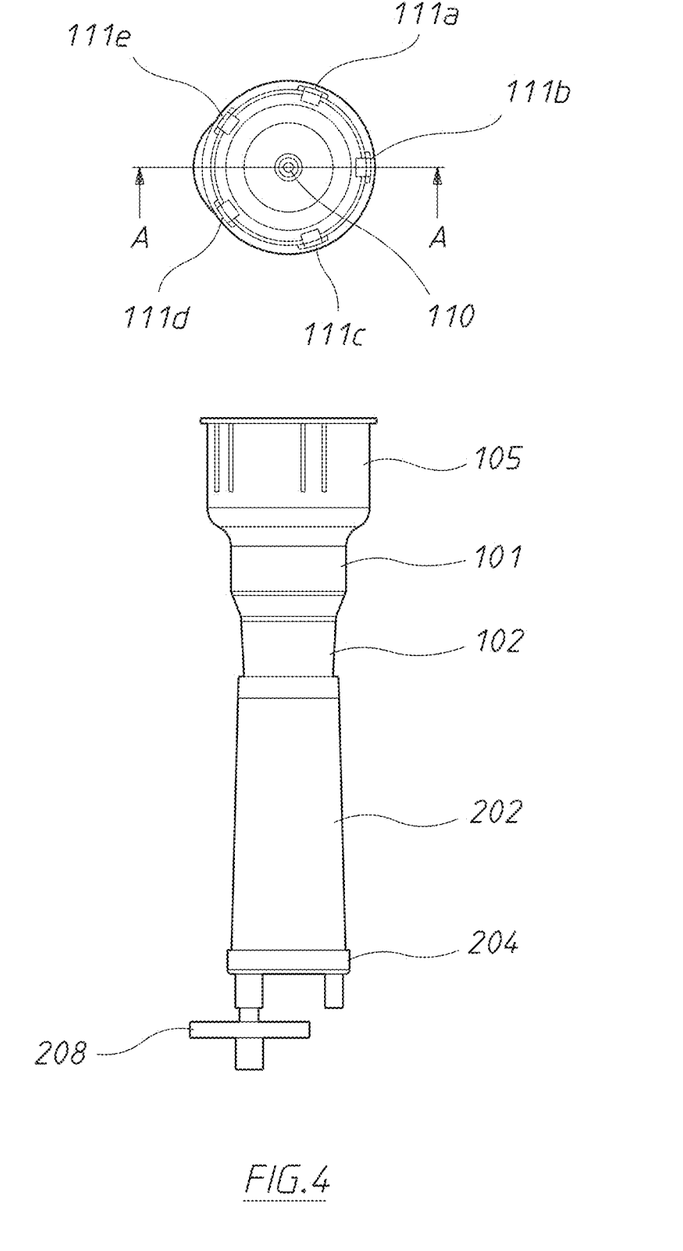
FIG. 4 is a top view of the device of FIG. 1.

Referring to FIGS. 1 and 2 there is shown a sampling device 100 including a body 101 having a sampling chamber 102 adapted to receive a liquid to be sampled. An inlet 104 on the body 101 allows liquid 103 to flow into the sampling chamber 102. A sampling port 105 on the body is adapted to receive a sample receiving container not shown in this Figure) for collecting liquid 103 from the sampling chamber 102 wherein the sampling port includes a safety shield 107 slidaby mounted to the inside 108 of the sampling port, the safety shield slidable between a blocking position in which access to the sampling chamber is restricted and an accessible position in which access to the sampling chamber is allowed.

The sampling chamber 102 includes a cylindrical hollow tube in the form of a sheathed needle 109 through which the liquid flows from the sampling chamber to the sampling port. The safety shield 107 prevents access to the sheathed needle until such time as a sample receiving container is inserted into the sample port.

It would be understood that the hollow tube that allows liquid to flow from the sampling chamber to the sampling port need not be a needle and could be any suitable tube adapted for the particular liquid that needs to be sampled.

The safety shield 107 includes an aperture 110 through which the needle 109 can move when the safety shield moves into the accessible position. That is, when moving from the blocking position to the accessible position, the safety shield slides down towards the needle, the needle passes through the aperture in the safety shield allowing the needle to engage with a sample receiving container thereby allowing a sample of liquid to be taken.

The safety shield is locked in the blocking position until a suitable sampling bottle is inserted into the sampling port.

In this embodiment, the locking means for locking the safety shield is provided by a plurality of locking clips or locking tabs 111 that prevent the safety shield from sliding down towards the needle and the base of the sampling port.

Five equally spaced locking clips 111*a-e* are located on the inside perimeter of the sampling port.

The locking clips are adapted to engage the shoulders of the sample receiving container thereby unlock the locking clips from the safety shield and allowing the safety shield to be pushed into the accessible position. In this position, the safety shield moves down and towards the needle, the needle passes through the aperture 110 thereby allowing a sample to be taken. The safety shield includes a spring 112 that forces the safety shield into the blocking position when the sampling bottle is removed. The locking clips automatically re-engage the safety shield once the safety shield is returned the blocking position. In another preferred embodiment, the needle is unsheathed and the safety shield includes a elastomeric or silicon stopper or septum in place of the aperture. In that embodiment, in order to keep the liquid flow path in the needle sterile, the cutting end of the needle is enclosed and sealed by the elastomeric stopper when the safety shield is in the blocked position. When the safety shield slides from the blocked position to the assessable position, the needle cuts through or pierces the elastomeric stopper allowing the needle to engage with the sample receiving container. When the safety slider slides from the assessable position to the blocked position, the elastomeric stopper once again encloses the cutting end of the needle and effective seals it against leaks and against the environment. The stopper is self healing due to its elastic properties or to it being in a state of compression so that when the safety shield slides from the assessable position to the blocked position, the cutting end of the needle is effectively enclosed and sealed against leaks and against the environment. As such the needle remains sterile.

Figure 5:
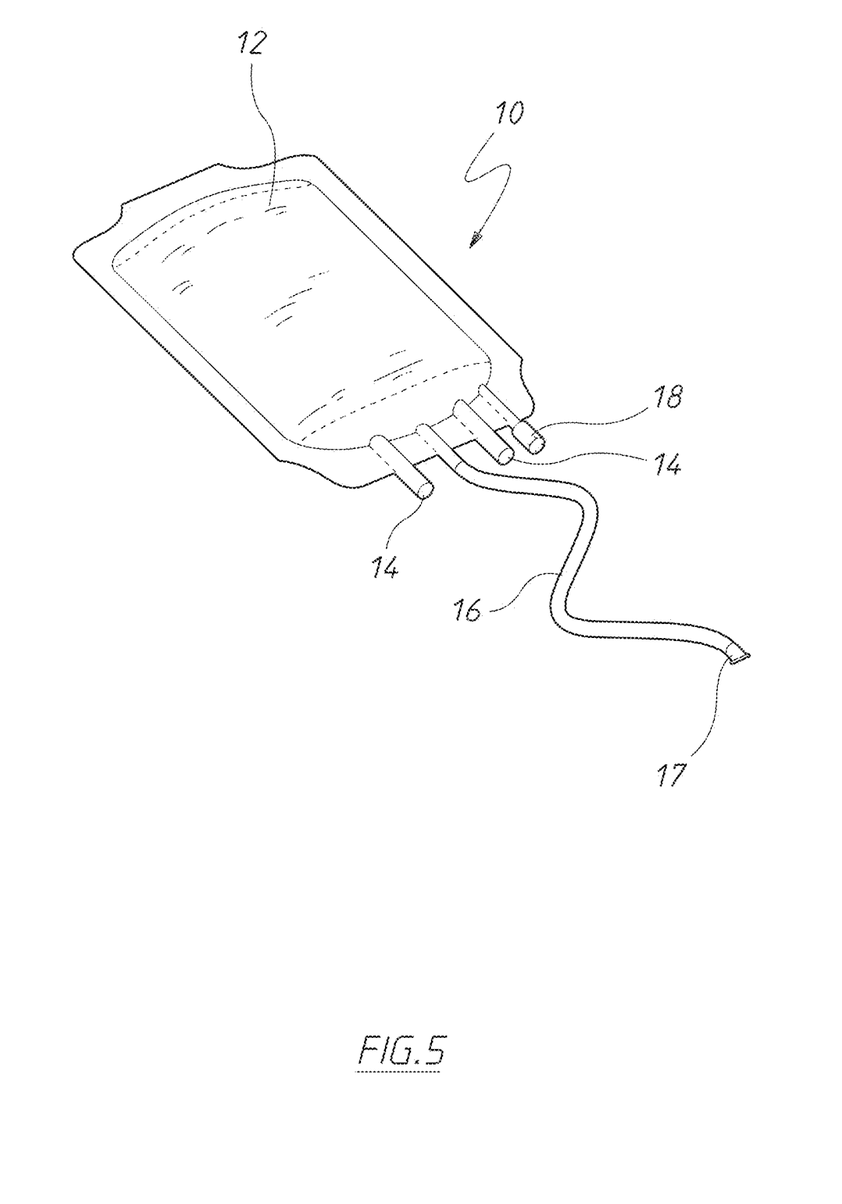
FIG. 5 is a liquid container according to the invention.
Figure 6:
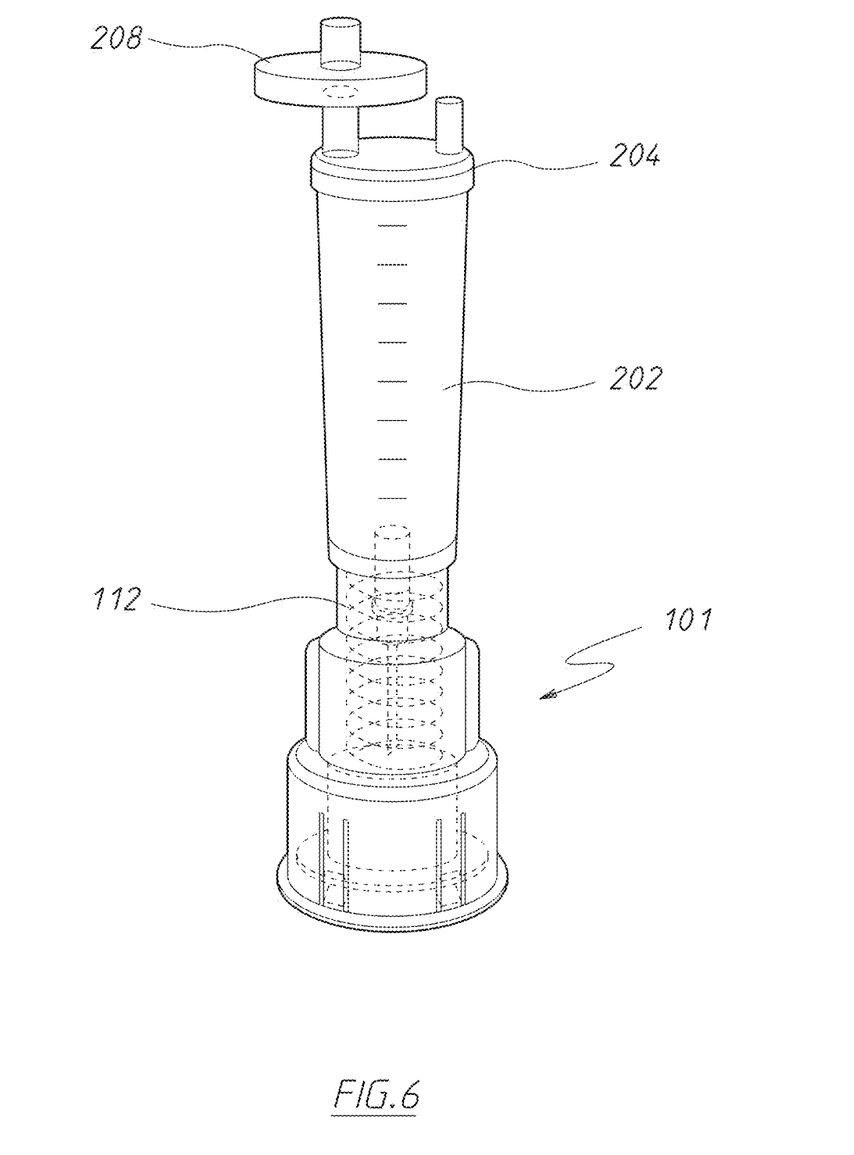
FIGS. 6, 7 and 8 and views of a device according to the preferred embodiment of the invention in use taking a sample.
Figure 7:
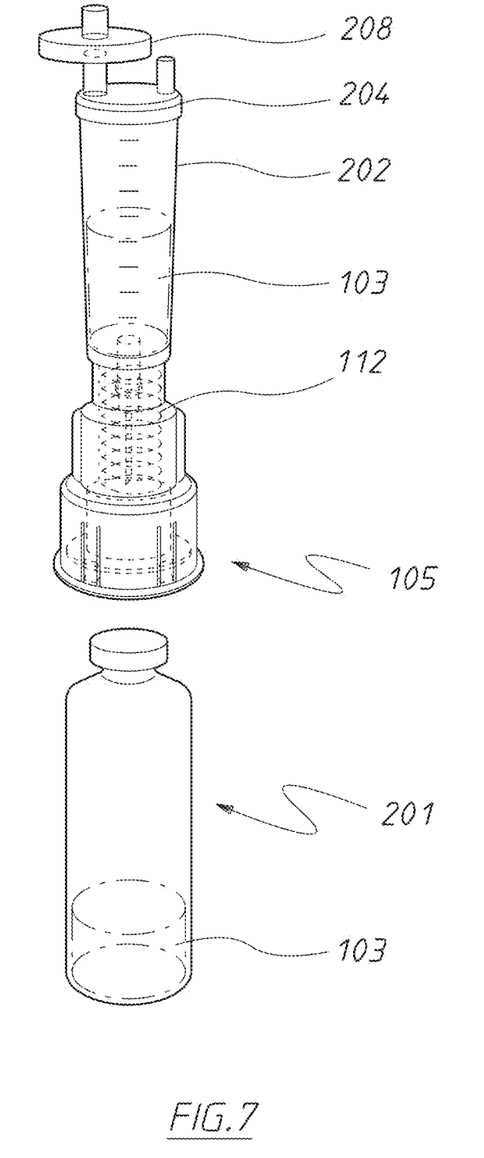
Figure 8:
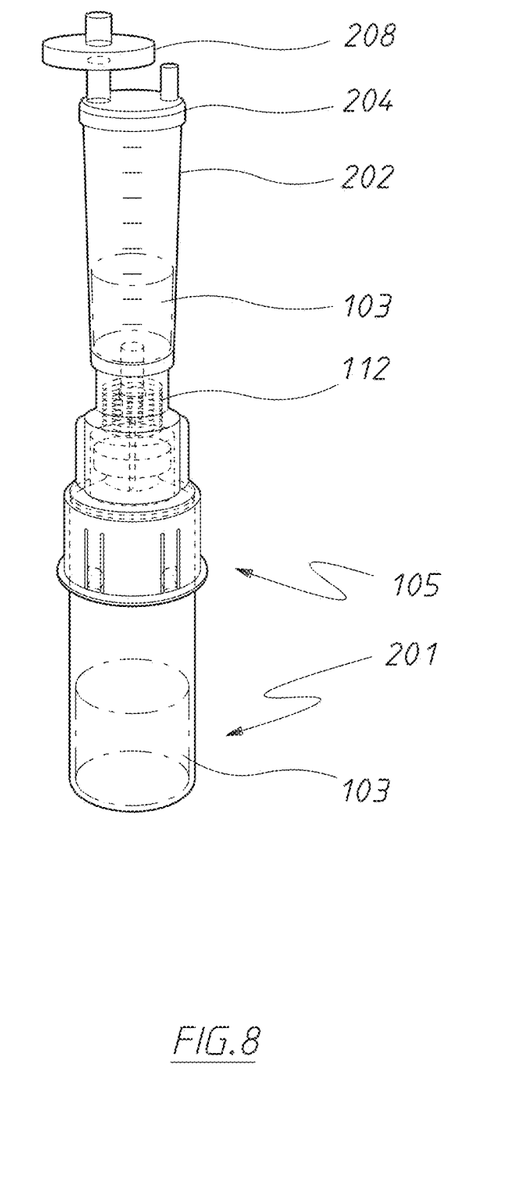
Figure 9:
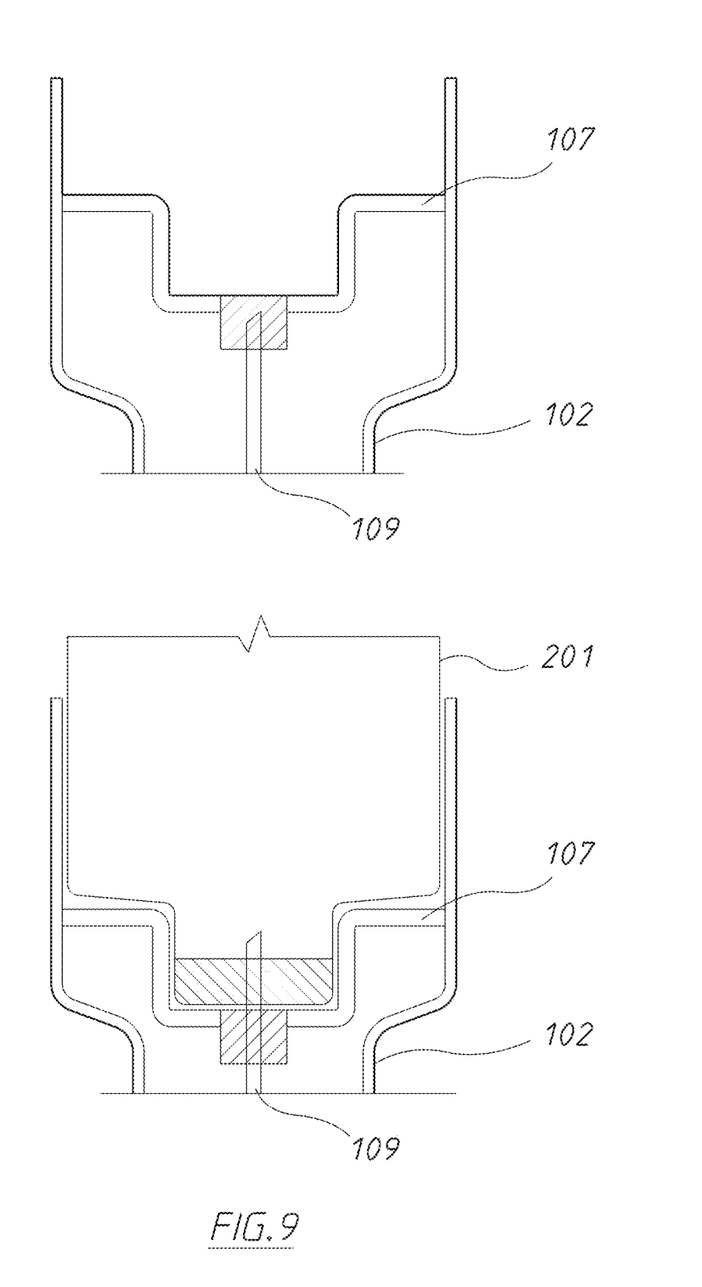
FIGS. 9, 10 and 11 show further embodiments of the invention.
Figure 10:
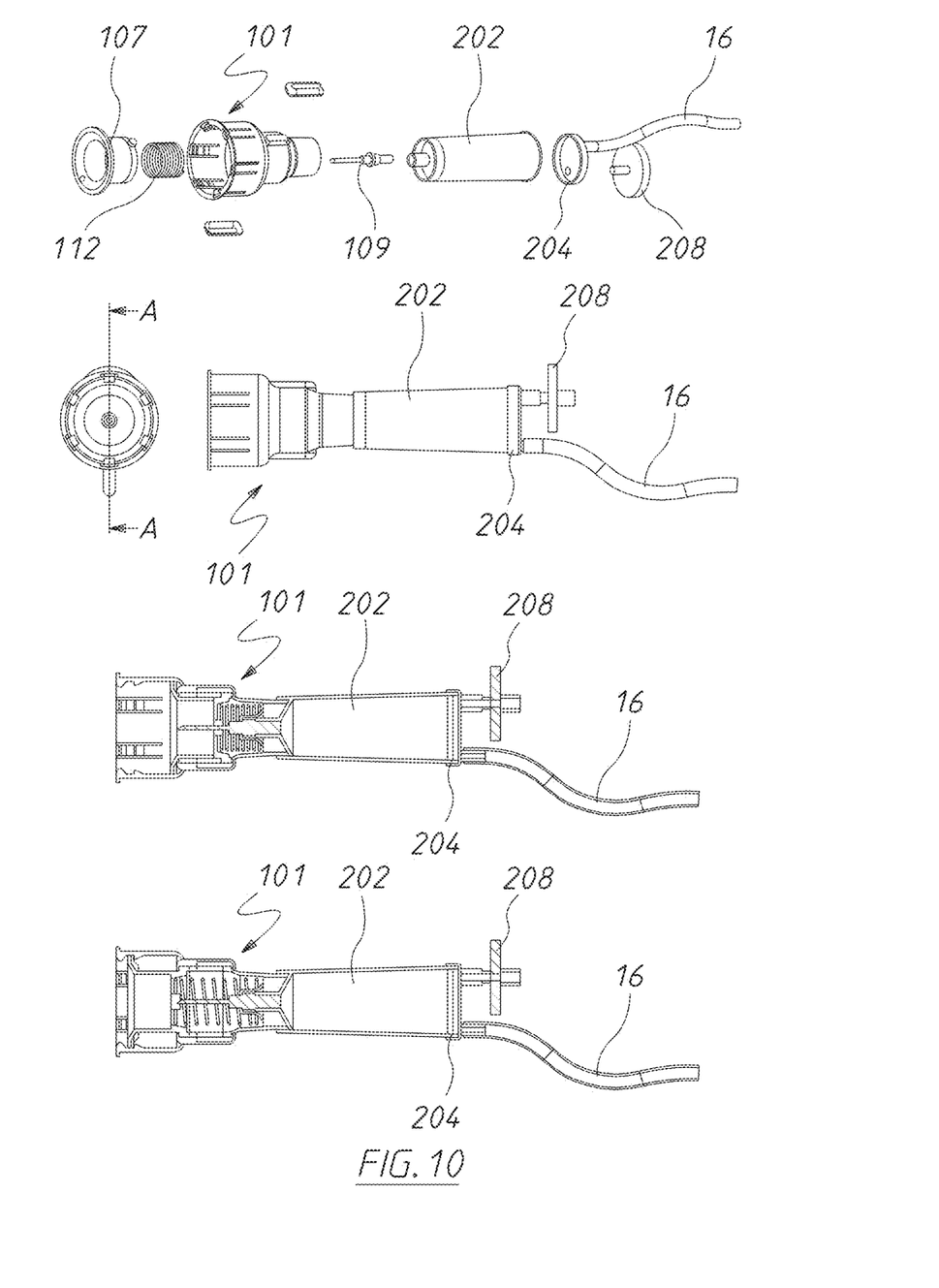
Figure 11:
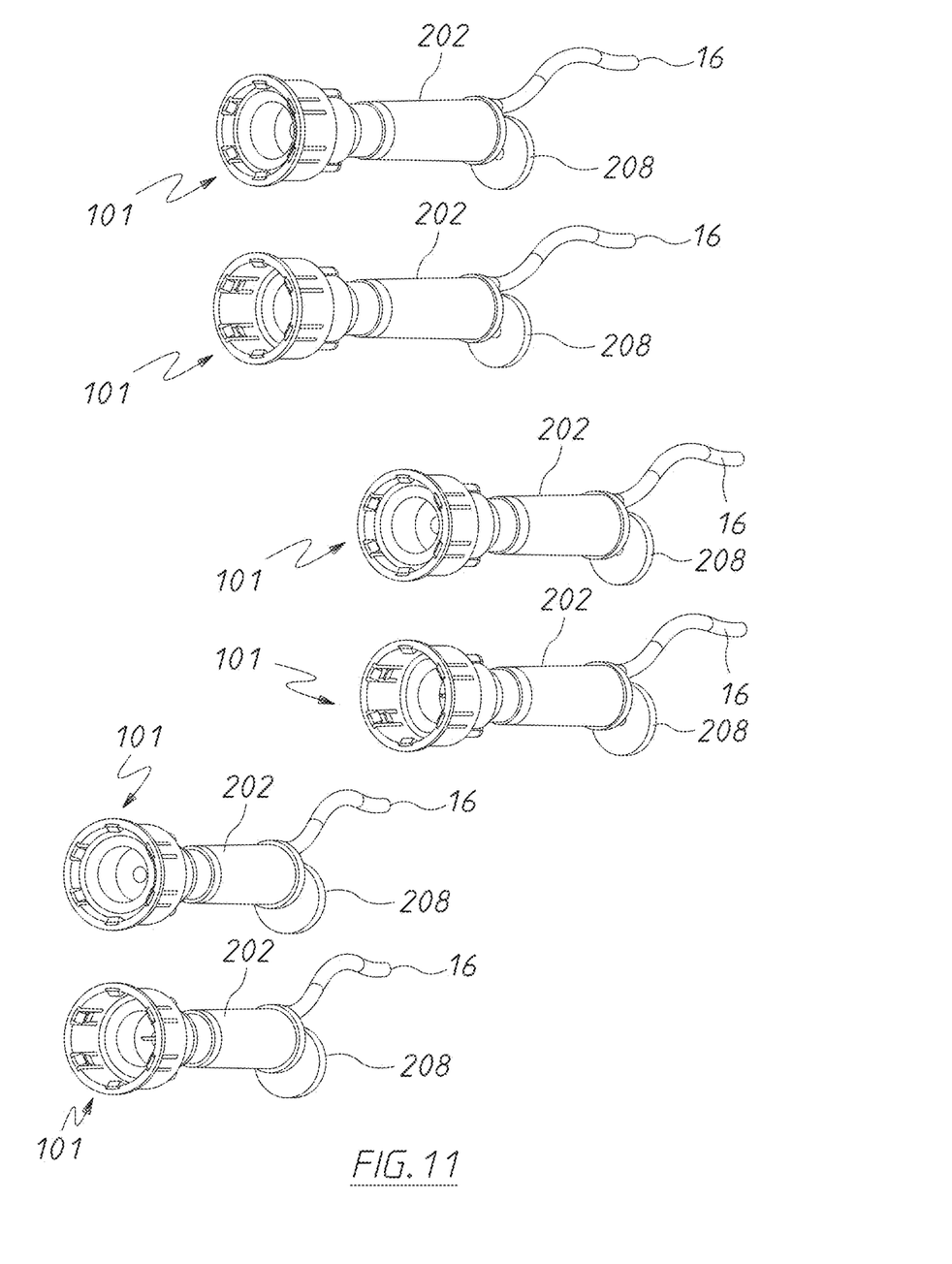

FIG. 5 shows a liquid container comprising a conventional sealed plastic pouch 10 containing a unit of platelets liquid, generally indicated at 12. Pouch 10 may have blanked-off tube connections 14 that may have been used during collection of the platelets but it will generally have at least one attached outlet or pouch tube 16 that is heat-sealed at its free end 17. Pouch 10 may also be provided with a split-septum needless port 18 through which a hollow blunt cannular can be inserted to extract samples of liquid 12. Samples of liquid may also be drawn from tube 16 by the use of a syringe and sharp medical needle. A already noted, both these methods of withdrawing samples involve contamination risk, both to the extracted sample and to the liquid in the pouch.

In some medical environments, a preferred embodiment of the invention is provided as part of a sampling kit for taking blood or platelet samples. Referring to the Figures and in particular FIG. 1*a* Apparatus 100 is supplied as a sterile unit and is unpacked by the health care professional at the time of use. It has a plastic inlet or sample tube that is that may be heat-sealed at its free upper (or distal) end and is fitted with a pinch clamp (not shown). Apparatus 100 also includes a tubular transparent and semi-rigid sight chamber 202 that has an open upper or distal end 203 closed by a closure 204 that has a first tubular spigot 205 connected to the lower or proximal end a of a sample tube (not shown) and a second tubular spigot 206 that is connected to filter 208 though which chamber 202 can be vented to atmosphere. Filter 208 is fitted with bacterial filter media (not shown) that allows air to pass but blocks the passage of bacteria.

Sight chamber 56 is conveniently formed from the transparent barrel of a conventional medical syringe that has appropriate volume graduations marked on its surface.

Sampling device 100 is rigidly connected to the sight chamber, thereby allowing fluid into the sampling chamber 102. Sampling device 100 is preferably molded from medical grade plastics.

In use, a user takes a sample receiving container 201 and places the sample receiving container into the sampling port 105. The sample receiving container engages the safety shield 107 and the user applies a force to counteract the spring 112 and move the safety shield from the blocking position into the accessible position. As the neck of the sample receiving container pushes into the locking shield it disengages the locking clips 111 thereby allowing the safety shield to slide into the accessible position. The needle passes through the aperture 110 and into the sample receiving container 201. The sample can then be collected by opening clamp 55 and allowing fluid to flow into the sampling device 100. Once the sample is collected, clamp 55 is closed, thereby shutting off the flow of liquid into the Apparatus 200 and allowing the user to remove the sample receiving container filled with the sampled fluid. Additional sample receiving containers can be used to collect additional samples as required.

When the sample receiving container is withdrawn from the sampling port, the spring 112 pushed the safety shield back into the blocking position, the locking clips re-engage the safety shield thereby securing the device.

According to another preferred embodiment, aperture 110 is replaced by a stopper in the safety shield. In this embodiment an unsheathed needle is used and the cutting end of the needle remains within the sealed position within the stopper when the safety shield is in the blocking position. When the safety shield is moved to the accessible position then the needle emerges through the stopper allowing it to pierce the receiving bottle/container. The needle end then returns to the sealed position within the stopper when the safety shield moves back to the blocked position. This ensures that the cutting end of the needle (more importantly the fluid flow path) never gets exposed to the external environment other than the stopper and inside the bottle/container during the taking of multiple samples.

While a preferred embodiment of the invention has been described and illustrated together with some variants, it will be appreciated by those skilled in the art that many other changes can be made without departing from the scope of the present invention as defined by the following claims.

The claims defining the invention are as follows:

1. A sampling device including:
    a body having a sampling chamber adapted to receive a liquid to be sampled;
    an inlet on the body for allowing the liquid to flow into the sampling chamber;
    a sampling port on the body adapted to receive a sample receiving container for collecting liquid from the sampling chamber thereby fluidly connecting the sample receiving container to the sampling chamber, wherein the sampling port includes a safety shield slidably mounted to the inside of the sampling port, the safety shield slidable between a blocking position in which access to the sampling chamber is restricted and an accessible position in which access to the sampling chamber is allowed, the safety shield including an aperture through which a needle can move when the safety shield moves into the accessible position, wherein the safety shield incorporates an elastomeric septum over the aperture on the safety shield so that in the blocking position a cutting end of the needle is enclosed and sealed from the external environment by the elastomeric septum thus allowing the use of non-sheathed needles for the sampling chamber, wherein the safety shield is locked in the blocking position until a suitable sample receiving container is inserted into the sampling port, and wherein the locking is provided by one or more locking clips, locking tabs or locking features that prevent the safety shield from sliding down towards the needle and the base of the sampling port.

2. A sampling device according to claim 1, wherein the sampling chamber includes a cylindrical tube through which the liquid flows from the sampling chamber to the sampling port.

3. A sampling device according to claim 2, wherein the cylindrical tube is a sheathed needle or unsheathed needle and the safety shield prevents access to the needle until such time as a sample receiving container is inserted into the sample port.

4. A sampling device according to claim 1, wherein the locking clips are located on the sampling port, or on the safety shield, or both.

5. A sampling device according to claim 4, wherein shoulders, or a neck or a cap or a lid or sides or other features of the sample receiving container unlock the locking clips thereby allowing the safety shield to be pushed back over the needle and thereby allowing the needle to pierce the sample receiving container lid or cap and allowing for a sample to be taken when the sample receiving container is inserted into the sampling port.

6. A sampling device according to claim 1, including a spring that forces the safety shield into the blocking position when the sampling bottle is removed.

7. A sampling device according to claim 1, wherein the locking clips automatically engage the safety shield once the safety shield is returned to the blocking position.

8. A sampling device according to claim 1, wherein the safety shield is restrained from exiting the sampling port by means of restraining tabs or features on the safety shield or locking clips or on the sampling port or a combination of the above.

9. A sampling device according to claim 1, wherein the safety shield includes a feature for gripping the sample receiving container thereby allowing the safety shield to be returned to the blocking position when the sample receiving container is retracted from the sampling port.

10. A sampling device according to claim 9, wherein the gripping features of the safety shield release the sample receiving container when the safety shield has returned to the blocking position.

11. A sampling device according to claim 10, wherein the locking clips automatically engage and lock the safety shield once the safety shield is returned to the blocking position.

12. A sampling device according to claim 11, wherein the safety shield is restrained from exiting the sampling port by means of restraining tabs or features on the safety shield or locking clips or on the sampling port or a combination of the above.

13. A sampling device according to claim 1, wherein the elastomeric material is in a state of compression to facilitate sealing of the needle.

14. A sampling device according to claim 1, wherein the movement of the safety shield from the blocking position to the un-blocked or accessible position allows the needle to penetrate the elastomeric material and thus to engage a cap of the sample receiving container, and the return of the safety shield to the blocking position returns the cutting end of the needle to the sealed position within the elastomeric material.

15. A sampling device according to claim 1, including an insert adapted on one end to fit in the sampling port and adapted on the other end to fit a sample receiving container wherein the insert disengages the locking clips thereby allowing a smaller diameter sample receiving container to be used with the sample port.

16. A sampling device according to claim 15, wherein the safety shield is mounted to the sampling port by one of the following methods: slidably mounted; hingedly mounted; or fixedly mounted.

17. A sampling device according to claim 1, wherein the sample receiving container is a bottle, a phial, a test tube, an evacuated tube, an evacuated bottle, a vacuum tube or other container.

* * * * *